(12) United States Patent
Blick

(10) Patent No.: US 11,054,967 B2
(45) Date of Patent: Jul. 6, 2021

(54) APPARATUS, METHOD, AND SYSTEM FOR CUMULATIVE REPORTING OF MEDICAL INFORMATION

(71) Applicant: Kenneth Blick, Edmond, OK (US)

(72) Inventor: Kenneth Blick, Edmond, OK (US)

(73) Assignee: CENTIBLICK, Edmond, OK (US)

( * ) Notice: Subject to any disclaimer, the term of this patent is extended or adjusted under 35 U.S.C. 154(b) by 361 days.

(21) Appl. No.: 15/970,356

(22) Filed: May 3, 2018

(65) Prior Publication Data

US 2018/0254095 A1 Sep. 6, 2018

Related U.S. Application Data

(63) Continuation of application No. 14/575,443, filed on Dec. 18, 2014, now abandoned.

(60) Provisional application No. 61/951,756, filed on Mar. 12, 2014.

(51) Int. Cl.
| | |
|---|---|
| *G16H 10/60* | (2018.01) |
| *G06F 3/0481* | (2013.01) |
| *G16H 15/00* | (2018.01) |
| *G16H 40/63* | (2018.01) |

(52) U.S. Cl.
CPC ......... *G06F 3/04817* (2013.01); *G16H 10/60* (2018.01); *G16H 15/00* (2018.01); *G16H 40/63* (2018.01)

(58) Field of Classification Search
CPC .... G16H 10/60; G16H 15/00; G06F 3/04817; G06Q 50/24

USPC .......................................................... 705/2–3
See application file for complete search history.

(56) References Cited

U.S. PATENT DOCUMENTS

| | | | | |
|---|---|---|---|---|
| 8,204,713 | B2* | 6/2012 | Blick | G16H 10/40 702/179 |
| 8,255,238 | B2* | 8/2012 | Powell | G01D 21/00 705/3 |
| 8,396,804 | B1* | 3/2013 | Dala | G16H 80/00 705/52 |
| 2002/0015064 | A1* | 2/2002 | Robotham | G06F 3/04883 715/863 |
| 2003/0177033 | A1* | 9/2003 | Park | G16H 10/60 705/2 |
| 2006/0149597 | A1* | 7/2006 | Powell | G06Q 10/10 705/2 |
| 2011/0231209 | A1* | 9/2011 | Maresh | G06Q 30/018 705/3 |
| 2013/0311193 | A1* | 11/2013 | Know | G06Q 10/00 705/2 |
| 2014/0249830 | A1* | 9/2014 | Gallopyn | G06F 19/00 705/2 |
| 2015/0356259 | A1* | 12/2015 | Park | G06Q 40/08 705/2 |
| 2018/0254095 | A1* | 9/2018 | Blick | G16H 40/63 |

* cited by examiner

*Primary Examiner* — Michael Tomaszewski
(74) *Attorney, Agent, or Firm* — Maier & Maier, PLLC

(57) ABSTRACT

According to an exemplary embodiment, a method, system, and device for providing cumulative reporting of medical information may be provided. The method, system, and apparatus may utilize software that provides access to any of a variety of medical records and/or medical data in real time and in a manner which allows it to be interpreted and shared. The method, system, and apparatus can also allow prompt alerts based on the interpretation of data shown.

16 Claims, 11 Drawing Sheets

900

APPARATUS, METHOD, AND SYSTEM FOR CUMULATIVE REPORTING OF MEDICAL INFORMATION

CROSS-REFERENCE TO RELATED APPLICATION

This application claims priority to U.S. patent application Ser. No. 14/575,443 filed on Dec. 18, 2014, entitled "Apparatus, Method, and System for Cumulative Reporting of Medical Information." and U.S. Provisional Patent Application No. 61/951,756 filed on Mar. 12, 2014, entitled "Apparatus, Method, and System for Cumulative Reporting of Medical Information." The contents of this application are incorporated by reference herein in their entirety.

BACKGROUND

Access to medical records and near-time or real-time medical data is typically difficult or impossible in most environments, often being unavailable even to medical professionals. While most physicians, practitioners, and patients own or have access to a laptop or desktop computer, or own a wireless device such as a smartphone or tablet computer that would be capable of displaying this data, few solutions exist to allow these parties to view, convey, share, and/or communicate medical results. This may impede physician, practitioner, and/or patient reporting and review of any desired types of medical information, something which can often be inconvenient and which can occasionally be detrimental to a patient's health.

Further, when access to the data is provided, it is often presented in a confusing manner. For example, medical information about a patient may be presented without putting it in the context of the patient's other medical information or the statistics of the broader population. This may impede rapid interpretation of the data, which may result in delayed assistance being rendered to a patient. Additionally, medical records and data are unable to provide viewers or necessary personnel with immediate alerts regarding the status or needs of a patient, which may likewise result in delayed assistance to a patient when it may be most necessary.

Lastly, patient medical records generally do not provide indications or notifications of when they have been or are being accessed. This presents potential security concerns, but also presents medical concerns. For example, it may be unclear when or if a patient's records have been accessed, which may make it unclear whether or not that patient is being attended to or not; this may present concerns for emergency patients who are in critical condition and who may be in immediate need of care.

Consequently, as discussed above, the present methods and systems of reporting medical results are in many ways deficient. Accordingly, there is a need for new methods and systems for reporting test results that solves some or all of the above-described deficiencies.

SUMMARY

According to an exemplary embodiment, a computer-implemented method for managing medical results may be provided. The method may include providing a device for presenting a graphical user interface to a user. The user may be a physician, practitioner, or patient. An electronic medical records server may also be provided and the device and user may be authenticated by the server. The device may request data from the server, which may then transmit the data to the device. The device may display the data through the graphical user interface in normalized decimal equivalent units. The user may be permitted to interact further with the displayed data through the graphical user interface.

According to another exemplary embodiment, a device for managing and displaying medical results may be provided. The device may include a display screen, a user input interface, a process, and a memory optionally linked to the processor, including executable instructions that, when executed by the processor, cause the processor to effectuate the following: access medical information, display the accessed medical information in normalized decimal equivalent unit form through a graphical user interface on the display screen, receive user input through the user input interface, and alter at least one of the graphical user interface and the accessed medical information in response to the user input.

According to yet another exemplary embodiment, a system for managing and displaying medical results may be provided. The system may include a device for managing and displaying medical results, as substantially described above. The system may further include an electronic medical records server. The device and the server may be communicatively coupled via a network.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION

Figure 1:
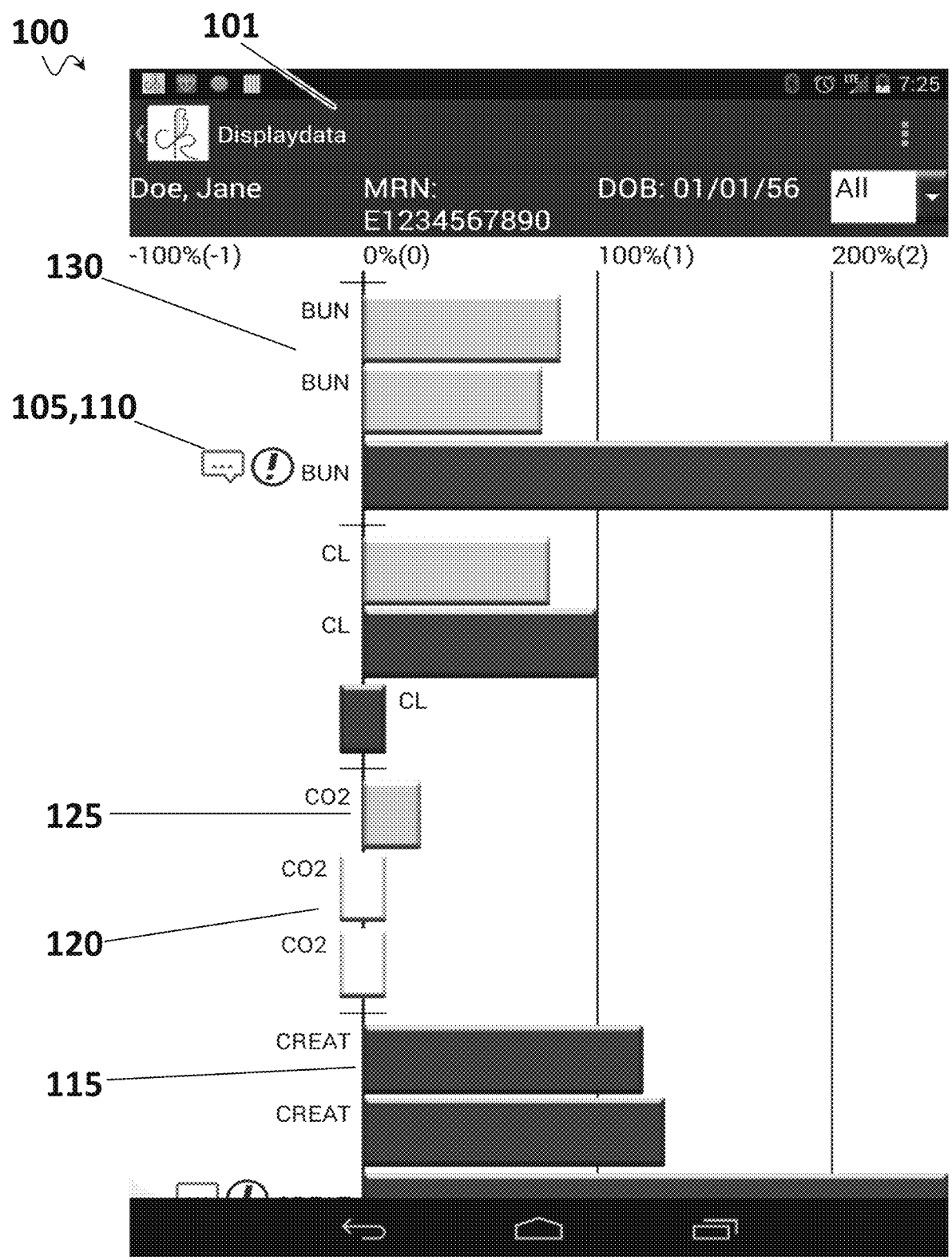
FIG. 1 is a GUI of an exemplary embodiment of software described herein.

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein may be described in terms of sequences of actions to be performed by, for example, elements of a computing device. It should be recognized by those skilled in the art that the various sequence of actions described herein can be performed by specific circuits (e.g., application specific integrated circuits (ASICs)) and/or by program instructions executed by at least one processor. Additionally, the sequence of actions described herein can be embodied entirely within any form of computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a computer configured to" perform the described action.

Generally referring to FIGS. 1-10, a method, system, and device for reporting medical results may be described. The method, system and apparatus may be embodied in any of a variety of manners, including software on a computing system (such as a laptop or desktop computer or a kiosk), a software application on a smartphone or like communication device, a network accessible software application or any other manner, as desired. Additionally, this description herein may utilize aspects of U.S. Pat. No. 8,204,713, entitled "Normalized Decimal Equivalent Systems And Methods," issued Jun. 19, 2012, the contents of which are hereby incorporated by reference in their entirety.

Elements of U.S. Pat. No. 8,204,713 describe some exemplary aspects of this description in more detail. Additionally, exemplary embodiments described herein may include physician, practitioner, and/or patient interactive software for the viewing, conveying, sharing and communicating of medical results. The software can include a dashboard and/or user interface for reporting any desired medical information on a computer display station, personal computer, and mobile wireless devices including handheld smartphones, tablets, and the like. It may further be appreciated that such software can be utilized on any device with display and network connectivity capabilities. Exemplary embodiments of software described herein may further have graphical displays, for example color graphical displays, and normalization of numerical information as described in the incorporated by reference U.S. Pat. No. 8,204,713. As described in detail in U.S. Pat. No. 8,204,713, medical information may be normalized by converting raw data to a decimal equivalent scale that facilitates reporting and analyzing the data.

Further, the software can facilitate physician, practitioner, and/or patient reporting and review of any desired types of medical information found in a typical medical chart (or electronic medical records system) with all results on the same normalized scale, in any desired numerical and non-numerical format. In an exemplary embodiment, the scale may be a CentiBlick Result (CBR) normalized graphic scale. A normalized graphical interface between a user and physician can provide data access, viewing and communication capabilities via click or touch screen functionality, as well as through any other user-device interaction, for example via stylus, mouse, voice command, or similar methods. The exemplary software may further present any desired medical information in a standard horizontal bar graph, as shown in more detail below with respect to the figures. Such views can include vertical and horizontal scrolling and various identifying features such as shading, patterns, or color graphics; for example, abnormal or positive findings may be presented as a red bar, borderline or indeterminate findings may be presented as a yellow bar, and findings or results in the "normal range" or desired range of are presented as a green bar. Other colors or visual representations and other data sets may also be included; for example, necropsy/autopsy reports may be presented as a blue bar. It can be appreciated that the colors used here are merely exemplary and any other desired color or visual indicia may be utilized to provide or convey information. Alternative graphical displays, for example, vertical bars or another desired orientation may also be selected depending on the user's preference. This may ensure that the data scales to the available display space, or can otherwise be displayed as desired. Other types of graphs or charts may also be utilized.

Still referring to the exemplary embodiments described herein, test results on the same test may be stacked into a data bar graph cluster with the most recent test being displayed on the top bar of the associated bar graph test cluster. According to at least one embodiment, a physician (or any other party) can elect in in the software preferences menu or elsewhere to have the most recent result at the bottom of the cluster, or to change the orientation or visual indicia in any desired fashion. This test cluster reporting can allow for a current test result shown on a top bar to be trended with previous results on this test, for example, by viewing the bar graph cluster showing previous results on the bars below. As one exemplary option, a physician can elect to have a line graph drawn tracing the displayed bar graph. By touching or clicking the data bar or otherwise interacting with the graphical display, the software may access and display data in the form of a traditional medical chart (for example, laboratory, vitals, and the like may be displayed in traditional form). Any of the following may be able to be displayed: standard, traditional reporting units, and laboratory method (e.g., Core Lab enzymatic, Point-of-Care (POC) i-Stat, etc. along with a corresponding normalized unit); comments regarding a reported result or results (for example a lab comment "hemolyzed sample"); a text report or medical image (for example a pathology report with a positive or negative cancer finding); a screening result (for example urinalysis); and/or a critical result requiring a physician's attention. Icons may be displayed on the device using the software that may also alert a physician that there are comments and additional details; alternatively, comments may be directly displayed without requiring a point and click or other selection. There may also be a critical result icon on the graphic display. Note that a physician, practitioner, and/or patient may be prompted to acknowledge that a critical result, medical report, or medical image was viewed using the above-described access option in order to return to the original graphical survey display. The date and time of a physician's review of the data, as well as any acknowledgements, may be recorded and displayed. A check or other indicia may be displayed next to the critical result flag, once viewed. Such a feature may be implemented using data from an electronic medical record (EMR) documenting the order entry and review loop cycle.

In still further exemplary embodiments, the system and software can also feature connectivity with medical records systems using HL7 standard formats (or any other desired format or formats) for information interchange using a push system approach for acute care critical results reporting and a user inquiry approach where a clinician/practitioner user is prompted to specify the inquiry parameters regarding a specific patient or group of patients. The push feature can send notifications to a mobile device, and may allow for stacking notifications when multiple critical reports are sent. The physician, practitioner, and/or patient may then touch a notification icon (or use any other access capability) to view the complete message or report.

In further exemplary embodiments, test results can be listed on a scrollable color bar graph display, for example in alphabetical order by test/procedure or specimen name (e.g., uterus), or through any other criteria desired. Test/report filters may be available when selecting this option, and a physician can filter the displayed color survey bar graph into any of a variety of formats, for example organ specific test/report panels (e.g., renal, liver, cardiovascular, uterus, etc.) in order to facilitate the diagnosis and/or to assist in monitoring the course of treatment, test/report panels designed for consults in a particular specialty area, and/or test/report panels designed for facilitating the generation of a discharge summary or encounter summary. With regard to discharge and encounter summaries, the system can aggregate various panels and data sets, looking for trends and progression during the course of care based on set statistical guidelines, describe the various data events observed by the expert software, and then aggregate these findings into a narrative report, along with diagnostic codes. The latter report can further include options to allow the physician, practitioner, and/or patient to review and edit this computer generated summary.

In an exemplary embodiment, a user may access a variety of options in the software using a double tap or any other selection technique. For example, a double tap of a mobile device screen displaying the software can display a menu of options including Confirm, Order Tests/Procedures, Call Floor, Call Patient, Email Patient, Text Patient, Release to Patient, Return, or other similar options. Also with a double tap or other selection, a "Physician Preference" feature can be set to allow the default laboratory results to be viewed in any of a variety of formats, for example formatted to non-CBR, non-graphically displayed results. Using this option, laboratory results, vitals, etc. can be viewed in the traditional, legacy spreadsheet format listing traditional values, units, flags, and normal/reference ranges.

Referring now to exemplary FIG. 1, a GUI of a mobile device illustrating the display 100 of normalized laboratory results using the normalized CBR system with the software described herein may be provided. Display header 101 may include, for example, the patient's name, the patient's date of birth, and other pertinent information; other information may be displayed on or beside the graph or elsewhere on the display, as desired. Icons or other attention-grabbing items may be incorporated as part of the display, for example to identify anomalous laboratory results or to identify patients in urgent need of care. Note, in this example, that critical results can include a "!" icon 105 and comments attached to the result can be indicated with a message icon 110. The user may be able to call up more information about why these or other icons are present, for example by selecting the result bar associated with the icons 105, 110 via touch screen or by mousing over the result bar, by clicking the result bar, by touching or mousing over other result bars 115, 120, 125 with which they are associated, or otherwise communicating selection information to the device. Abnormal results may be shown with a uniquely identifying shading, color, or pattern such as that shown in bar 115. Borderline results may be shown with a different shading, color, or pattern, as shown in bar 120. Normal results may be shown with yet a different shading, color, or pattern, as shown in bar 125. Results on the same test, such as BUN, may be stacked or aggregated in the display; the exemplary embodiment of FIG. 1 displays these results in a result cluster 130, with the most recent test displayed on the topmost bar.

Figure 2:
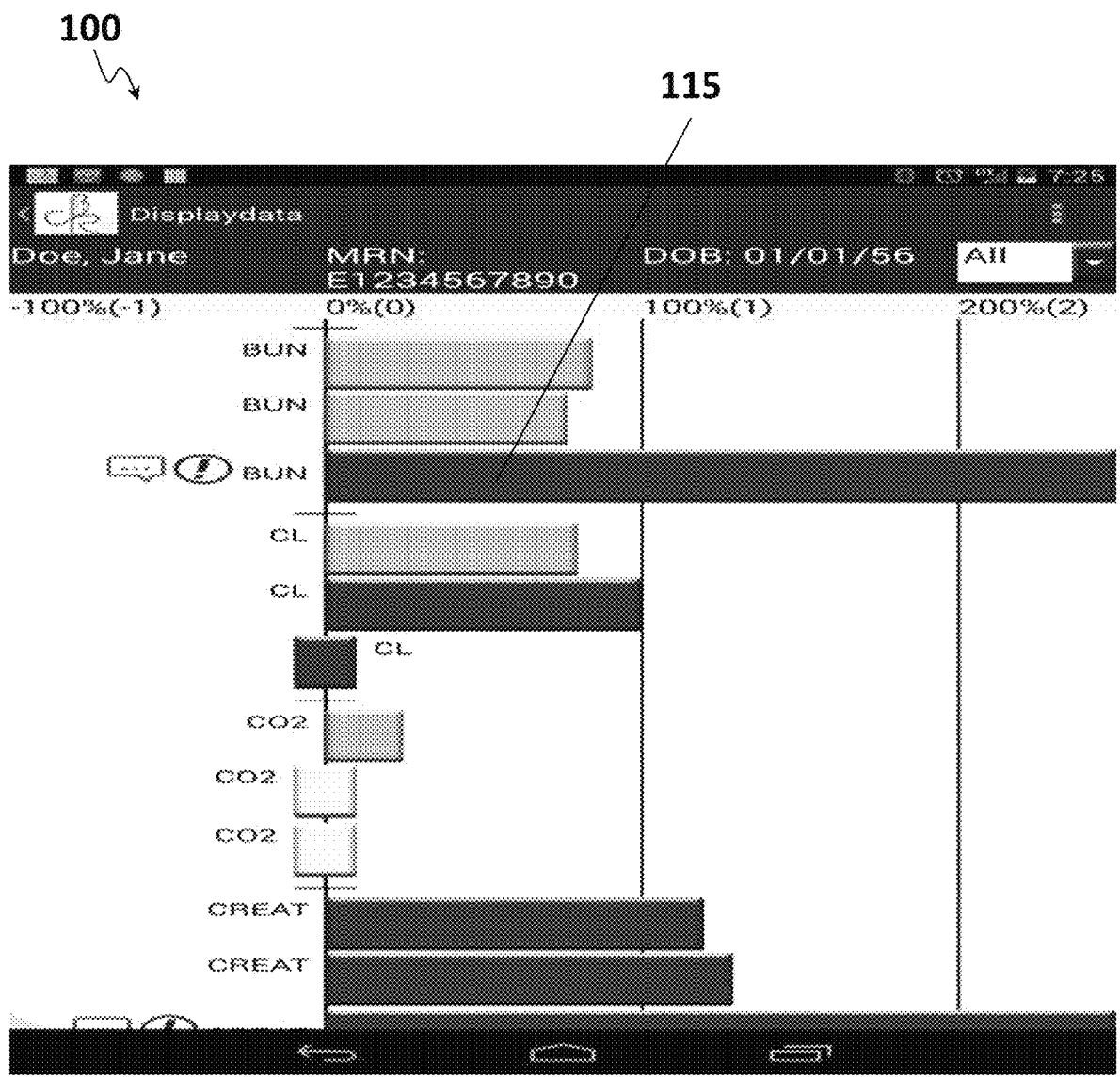
FIG. 2 is an exemplary depiction of a user interacting with software described herein.

Exemplary FIG. 2 provides a mobile device showing a display 100 similar to that of FIG. 1. A user of the software, such as a physician, practitioner, and/or patient, may select one of the graph elements, such as bar 115 shown in FIG. 2, to gain access to additional data about the test that the bar 115 corresponds to. For example, touching or clicking the bar 115 may allow the user to view a comment attached to a result, identify why a result has been flagged with a warning icon for critical results, or view the traditional reporting units and normal ranges for the test in question.

Also, as represented in FIG. 2, the display 100 may provide for cumulative reporting, showing progression from previous tests to more recent tests. This may be shown by multiple graph elements. In exemplary FIG. 2, a series of graph elements may be shown for each test, progressing in chronological with the most recent appearing at the top. In exemplary FIG. 2, the patient may show a high BUN and Creatinine level during an earlier test, indicating a critical situation such as renal failure, but as indicated by the progression of the tests, the patient may be shown to be trending toward normal values. The reporting showing the progression of various tests may be in the form of lab clusters, such as a BUN cluster. Each test may be represented in a cluster of graph elements showing a patient's progression. In an exemplary embodiment, as shown in FIG. 2, the most recent results of each cluster may appear at the top of the cluster.

Figure 3:
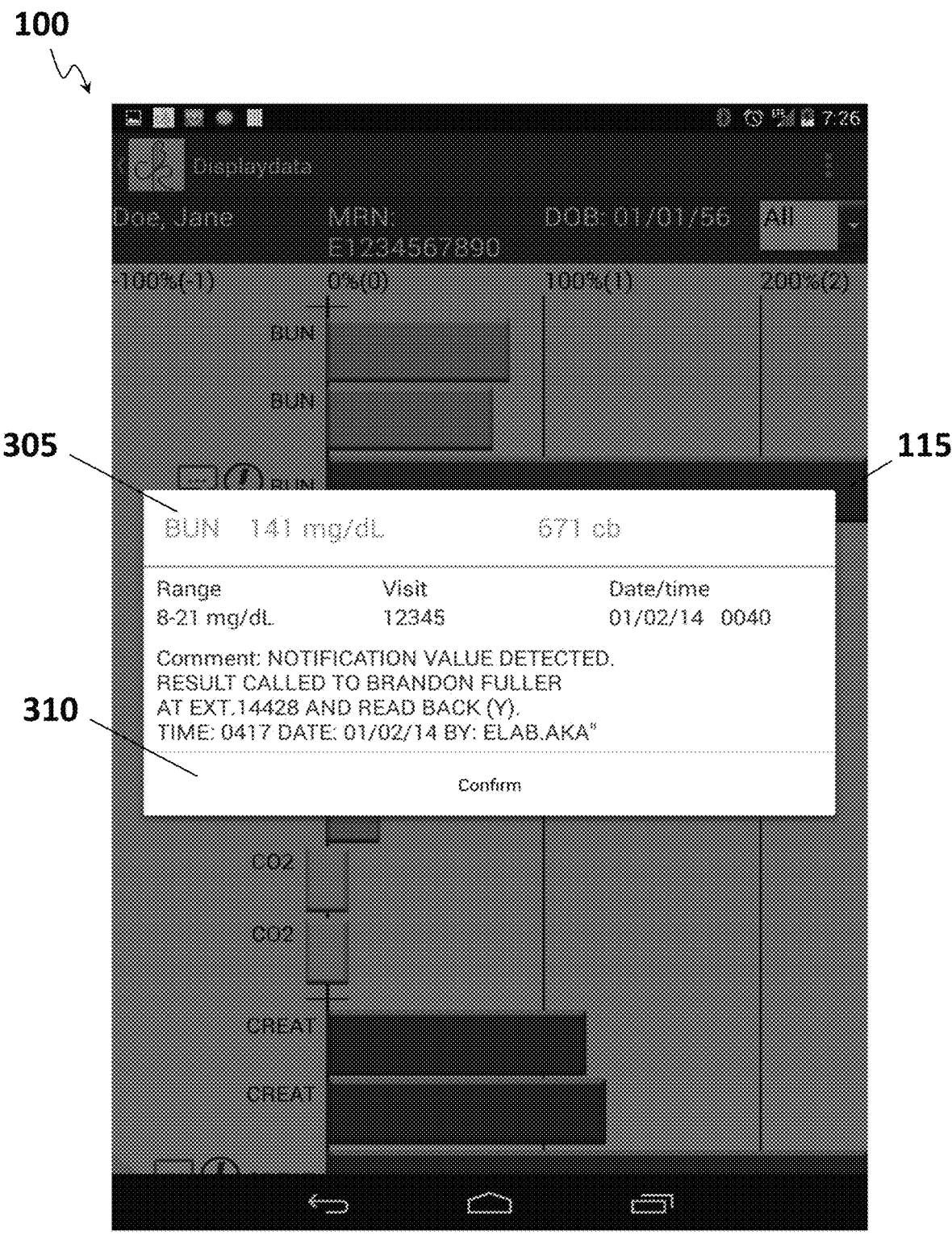
FIG. 3 is a GUI of an exemplary embodiment of software described herein.

Exemplary FIG. 3 provides a GUI showing an access view 305 of traditional laboratory results, such as might be displayed when bar 115 in exemplary FIG. 2 is clicked, touched, or otherwise accessed. The exemplary embodiment of FIG. 3 shows the traditional result of 141 mg/dL along with the normalized CBR of 671 cb. This screen 305 may also show other information about the test, such as which laboratory the test was performed in, along with unique normal ranges associated with the method in that laboratory. Access view 305 may display the comments associated with the red bar 115 if any are available; for example, the comment attached to the result displayed in FIG. 3 documents that this high result is critical for the patient and therefore the result was called to an attending physician. According to the exemplary embodiment of the access screen 305 displayed in FIG. 3, the physician, practitioner, and/or patient must select confirmation button 310 or otherwise confirm that they viewed this critical result. The mobile device can log the date, time and the identity of the physician, practitioner, and/or patient confirming this critical result on the device and may also append a green check icon (or other indicia) next to shown icons.

Certain tests may also be given a higher or lower priority or may be received differently by the device; for example, the result shown in FIG. 3 was critical for the patient and as a result may be "pushed" to an attending physician and shown as a notification on the mobile device. This latter feature may be particularly beneficial for personnel associated with an emergency department, as they may be caring for multiple critical patients at the same time, and may need lifesaving vitals and laboratory data of a critical nature in real-time for those patients. The software on the device may also be set to alert an attending physician or practitioner of this critical result alert message by, for example, sending a notification to the physician's pager or other mobile device.

The software may have additional functionality other than merely displaying the results. For example a physician, practitioner, and/or patient, after instructing the software to display the critical results on an access screen 305 or otherwise, may be given other options, such as prompts to order another test or procedure, call the floor or patient, email or text another practitioner or the patient, and/or forward the result to the patient Similar results and other options may be available from the home display screen 100 or may be otherwise available. The physician may also be able to select an option indicating that they viewed the entire screen of transmitted data. Data that has been previously viewed may have this indicated on the home display screen 100 by an alteration of the display or other indication. For example, previously viewed and confirmed data on a cumulative stacked bar report may shade the previously viewed bars with a darker shade than the new and unconfirmed CBR bar on the top of the data cluster. This function may be dependent on verification order review loop data from the EMR order entry system. Alternatively, any other manner of marking previously viewed bars may be utilized, as desired.

Figure 4:
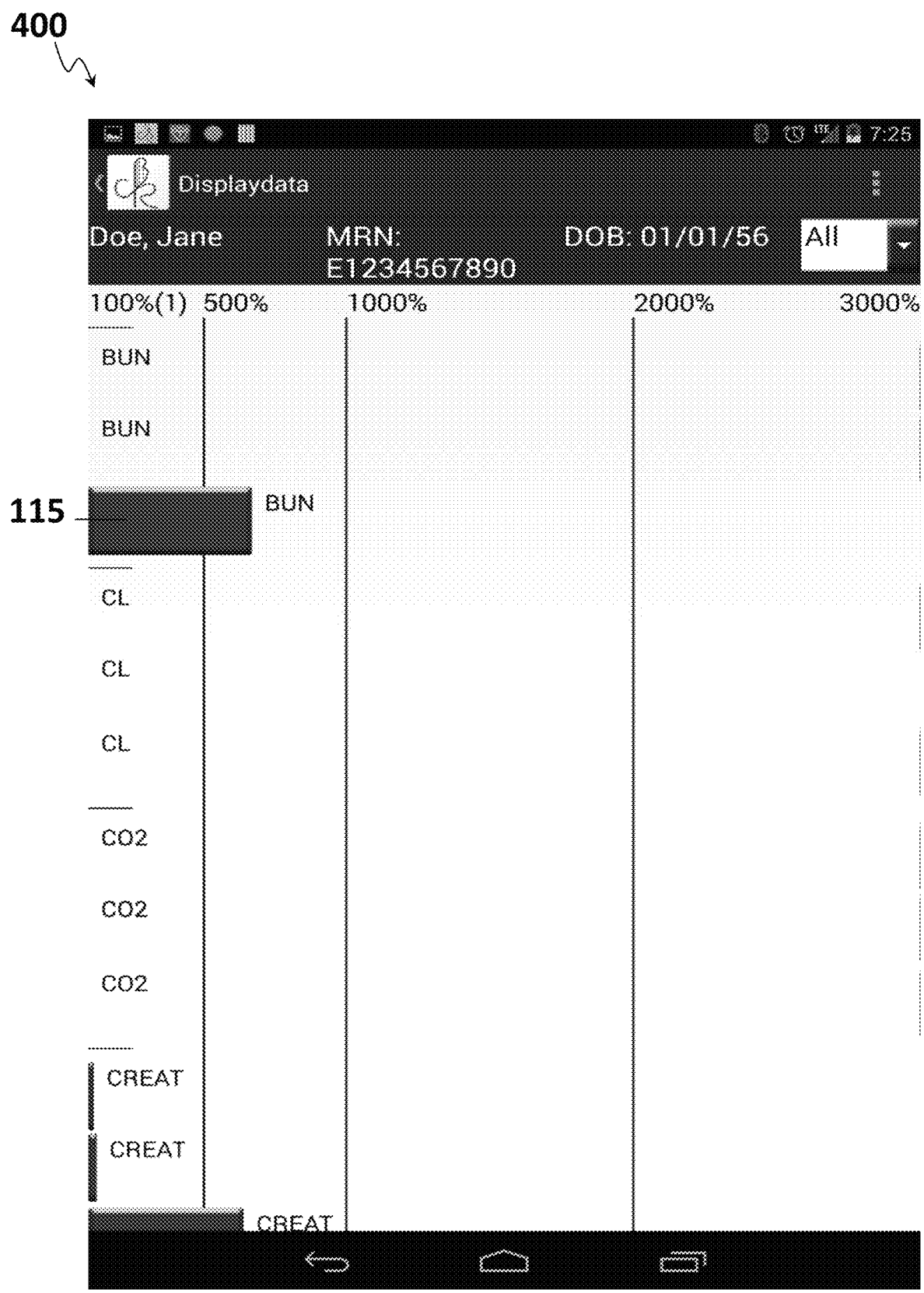
FIG. 4 is a GUI of an exemplary embodiment of software described herein.

Exemplary FIG. 4 provides a GUI showing an overflow screen 400, corresponding to the data displayed in FIGS. 1 and 2. The overflow screen 400 features the BUN red bar 115 displayed in those two figures; the bar 115 corresponds to a value greater than 200% of maximum, which may make it unreadable on an unaltered display as in FIGS. 1 & 2. This exemplary view may be obtained by swiping the screen with a right to left motion, by using another common scroll-to-the-right feature, or by using any other access capability, as desired. According to some embodiments, CBR normalized scales may be able to be adjusted either instead of or in addition to the use of a scroll-to-the-right feature; for example, a user may be able to zoom in and out of the CBR normalized display featured in FIG. 2. As shown in exemplary FIG. 3, and according to some embodiments, the physician, practitioner, and/or patient can view results at any time from a pick list of stored results on the device, if desired. Likewise, according to some embodiments, a user may be able to return to the original CBR screen shown in exemplary FIG. 3 by swiping with a left-to-right motion, or by taking other action, as desired.

Figure 5:
FIG. 5 is a GUI of an exemplary embodiment of software described herein.

Exemplary FIG. 5 provides a GUI showing an exemplary inquiry screen 500 where a physician, practitioner, and/or patient can "pull" or retrieve results from a medical database based on patient identifiers in a HIPPA-compliant manner. Various filtering options can be included; for example, a filter may allow a user to search for a patient based on a date range corresponding to the patient's last visit to a physician, or may allow search filtering based on any other factor, as desired. This may allow current results to be displayed graphically as in exemplary FIG. 1, and, in the context of previous results, may allow trends in results to be readily observed by a user. Where applicable, trends may also be identified by the software, either automatically or following an identification procedure that a user may execute, as desired. Critical results requiring action may also be readily identified, either automatically by the software or by the action of the physician, practitioner, and/or patient. An embodiment of this device may be configured particularly for patients, to reflect the fact that patients may now legally order and receive selected laboratory results in real-time from select commercial laboratories (e.g., LabCorp, Quest); such an embodiment may report test results in a readily interpretable, intuitive manner. Alerts and comments may also be presented in a fashion that may be interpreted directly by patients; for example, a patient-oriented embodiment may use different or less professional language, or may provide recommendations to the patient about their suggested future conduct. This may provide patients with more responsibility for their own individual care and health monitoring. Such alerts could, for example, notify patients to go immediately to the emergency department (i.e., a critically low potassium, high INR, etc.) or, for less critical test results, contact their physician for an appointment.

According to an alternative exemplary embodiment of the inquiry screen shown in FIG. 5, laboratory results, vitals, images, pathology reports, and the like may be listed as a line item when a name or identifier is entered on the screen or otherwise searched for. All specimen results may be listed and selectable, or, alternatively, if a user searches for or identifies a particular visit (such as by inputting a visit number into the appropriate search prompt), all specimen results for that visit may be listed and selectable. Some or all results may be able to be selected, grouped, and displayed on the screen shown in exemplary FIG. 2. Data regarding individual visits may also be displayed and selected in its entirety, with laboratory data, vitals, etc. corresponding to that visit displayed for review on a screen similar to that shown in exemplary FIG. 2. Also, multiple visits or encounters with the patient can be grouped and displayed on a screen similar to exemplary FIG. 2, which may allow trending of results across visits or other useful interpretation of the data. Also, if desired, laboratory data, reports, etc. can be stored on the device, for example in a local cache, to allow for quick retrieval and so that results review and trending of results can occur on the local database. Locally stored test results may be reviewed by a patient or physician using the device. The user of the device may select a visit test item from a sequential list of stored lab results, which were previously transmitted to the device.

Figure 6:
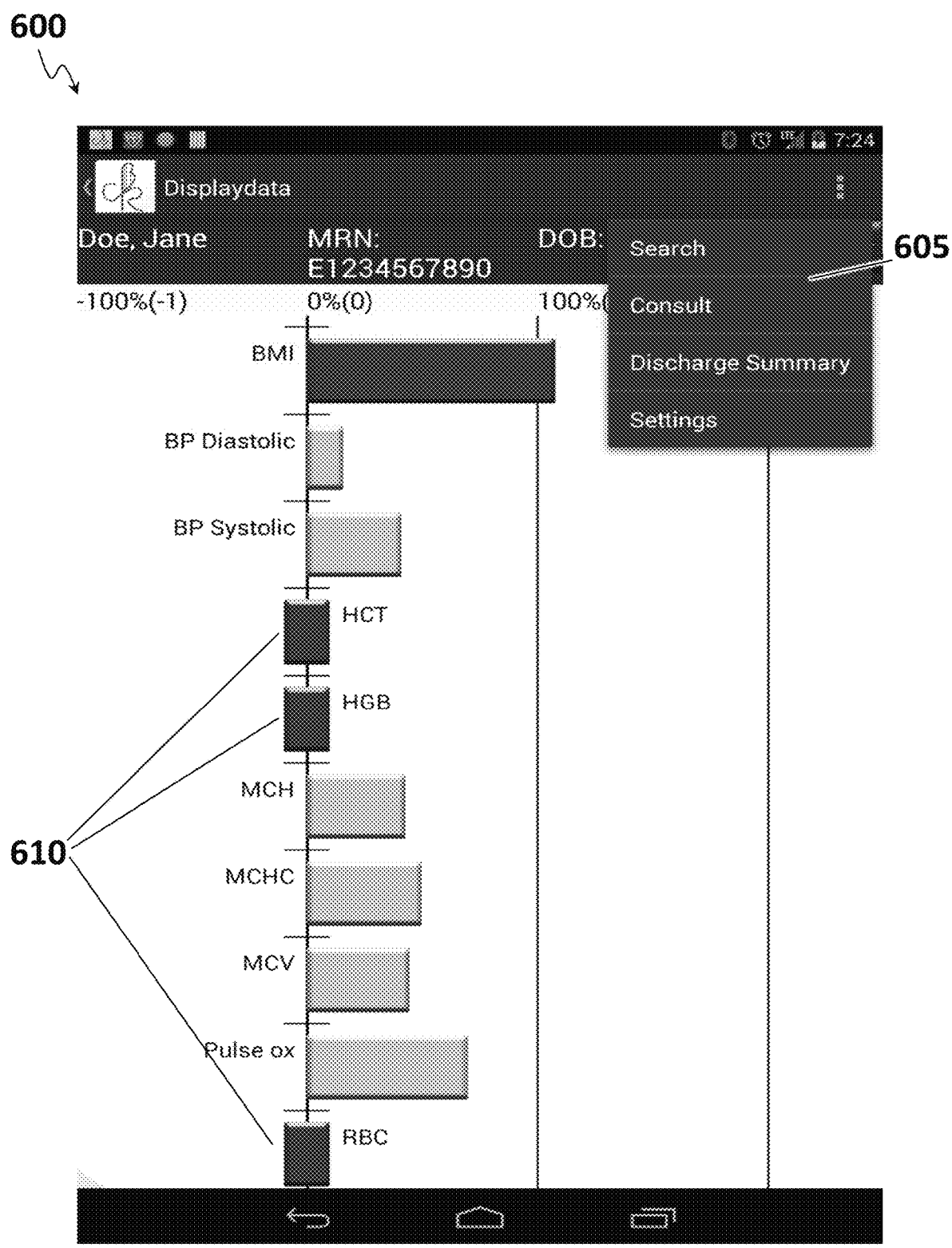
FIG. 6 is a GUI of an exemplary embodiment of software described herein.
Figure 6A:
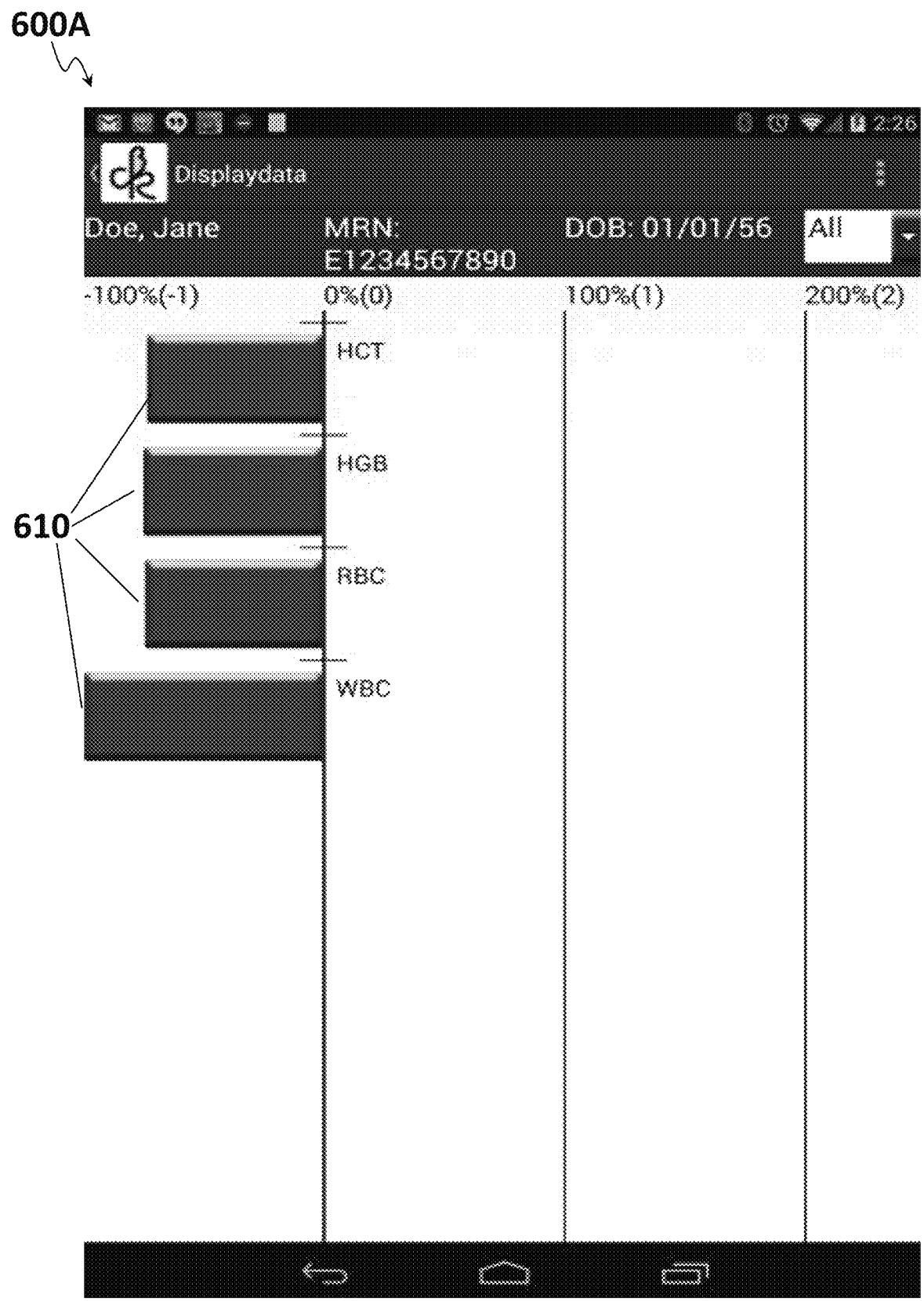
FIG. 6A is a GUI of an exemplary embodiment of software described herein.

Exemplary FIG. 6 provides a GUI 600 showing the ability of the user to trigger various pre-programmed filters to the data. Specifically, exemplary FIG. 6 shows an "anemia filter;" which may be selected or employed to display test results that may be relevant to making a diagnosis of anemia. This may include, for example, test results from a complete blood count (CBC) along with some selected vitals. As in previous examples, the HCT, HgB and RBC, which are all below normal levels in this instance, may all be reported with red bars 610 indicating low or below normal results. Other test results may also be reported as in previous embodiments. A menu, such as a drop-down menu 605, may also be available to users; this may allow those users to search for specific tests (either within a currently filtered set or for a certain patient in general), and to consult filters, and may enable software support for constructing written narrative consults based on practice specialty when appropriate. Another feature available from the menu 605 may be a discharge summary support facilitating a CBR driven chart review feature, which may note abnormal results, trends during care, procedure and diagnostic coding support, and written narrative support based on expert systems software and statistics. Pre-programmed filters may be accessed and modified through this menu, such as via the settings option;

other functionality may also be included, such as general device or software settings. Filtered data may also be further filtered, for example to show only problematic test results or test results lower or higher than optimal; FIG. 6A provides an additional exemplary GUI showing this functionality. In FIG. 6A, the filtered test results displayed in FIG. 6 have been further filtered using a "hematology" filter, which may be shown in FIG. 7, to only show those test results with values below the normal lower bounds for the population and consistent with anemia, which may be used as the basis for a diagnosis or a treatment regimen.

Figure 7:
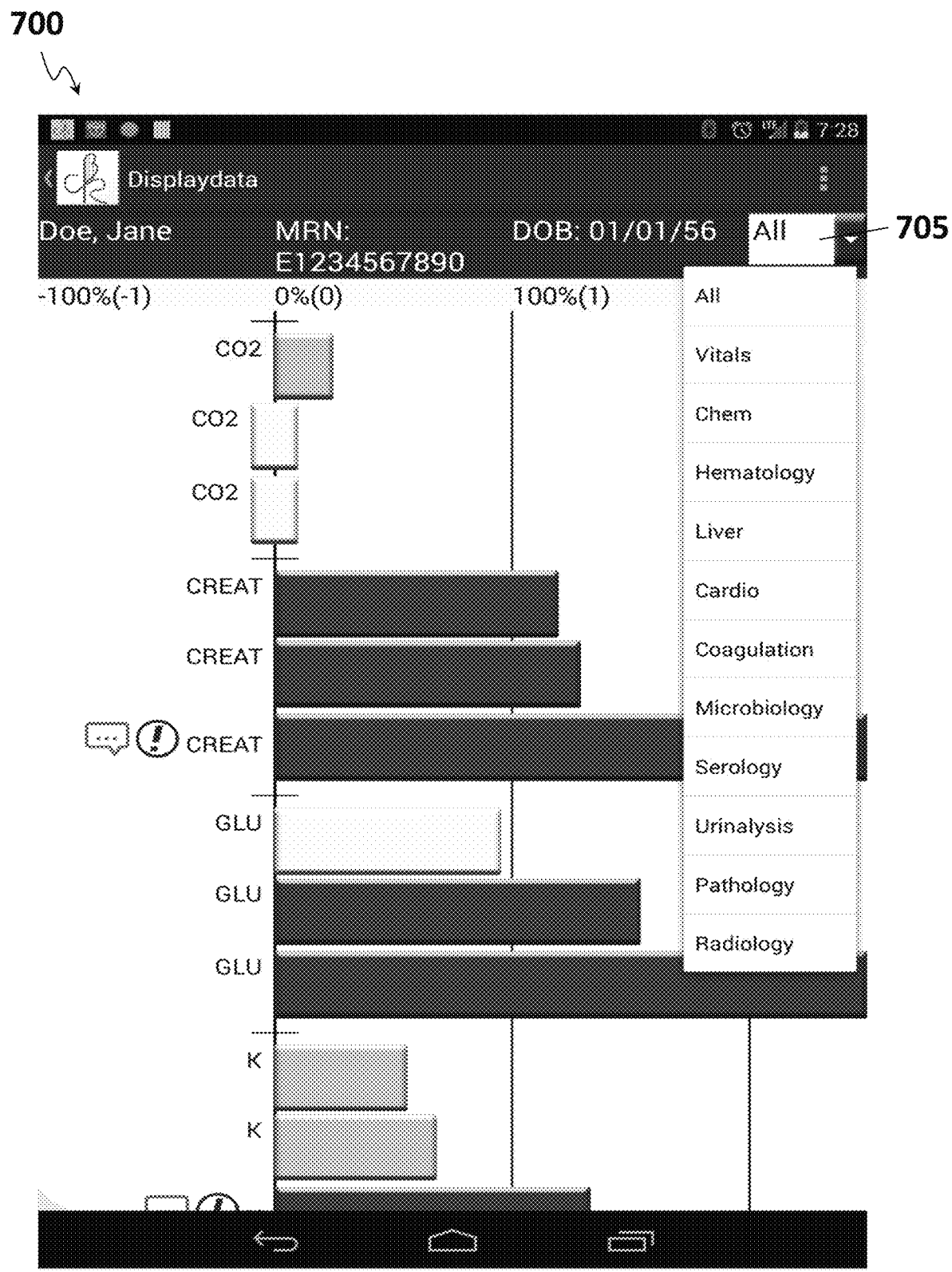
FIG. 7 is a GUI of an exemplary embodiment of software described herein.

Exemplary FIG. 7 provides a GUI 700 showing a selection of test results, vitals, and the like. FIG. 7 displays a drop-down menu 705 displaying various filters that may be applied to the data to show only those test results relevant to certain lab sections, certain potential diagnoses, or as desired. In this instance, drop-down menu 705 shows that the "All" option has been selected, which may cause the device to display all test results available for the patient in question (herein identified as "Jane Doe"), in alphabetical order or according to another organizational schema. A user may be able to select an alternative filter, such as "Vitals" or "Chem," to show a different selection of test results. Other exemplary filters may include blood pressure and heart rate. Preprogrammed pull down filters may be touched, clicked, or selected as desired, and the various views of the medical data can be displayed in the CBR stacked graphical bar format, or any other format, as desired. Data views may be pre-generated and stored or may be generated and displayed in real time. According to an exemplary embodiment, all laboratory data may be presented in normalized data clusters by test name regardless of the laboratory or method used to generate the result. For example, by touching or clicking the "Cardio" filter option, various cardiac specific tests (CPK, CK-MB, troponin-I, etc.) along with vitals can be immediately shown to the physician or practitioner.

Figure 8:
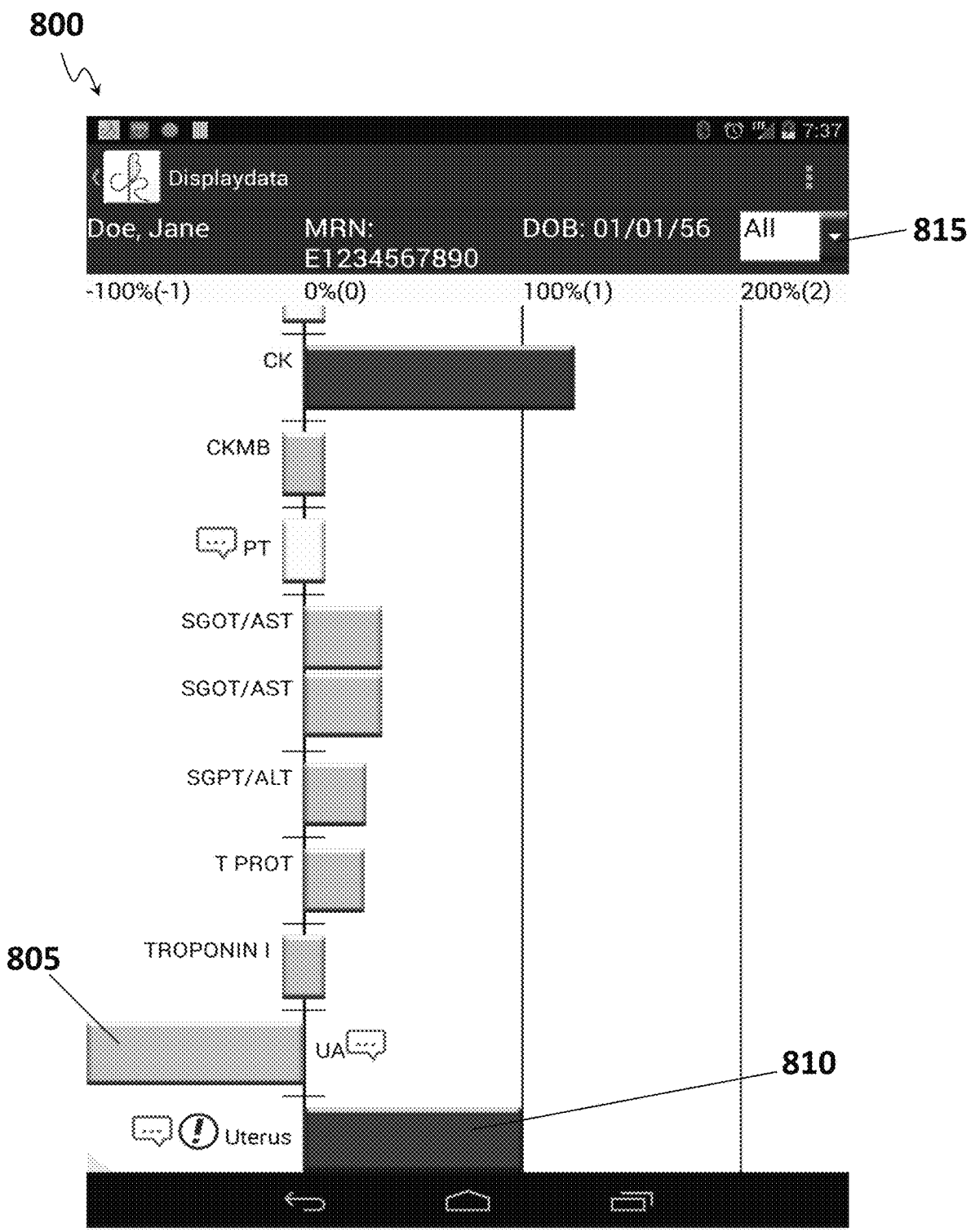
FIG. 8 is a GUI of an exemplary embodiment of software described herein.

Exemplary FIG. 8 provides a GUI 800 which may show how results of non-numeric laboratory tests and studies in anatomic pathology may be reported graphically as part of the overall normalized CBR system. Tests with, for example, a binary "true/false" or "positive/negative" result may be reported by using bars similar to those used for the numeric laboratory tests; however, bars for non-numeric tests may use different methodology. For example, bars for non-numeric tests 805, 810 may have fixed lengths corresponding to a positive and negative result, a different graphical representation, or a different or reversed color scheme that may serve to more clearly identify the displayed result as representing a binary test. As shown at the bottom of the screen, a negative urinalysis report with a green bar 805 of fixed length −100% extending to the (−1) left side of the screen is reported while a red bar 810 of fixed length +100% indicating a positive (+1) result was observed for a uterus specimen in this example, the latter being dissected in surgical pathology as part of a complete hysterectomy case. Further access with respect to these bars can allow the physician or practitioner to review the entire report. Note that, in the exemplary embodiment displayed in FIG. 8, the "All" option 815 is selected, which may display all test and pathology results for a given patient in alphabetical order; as in previous embodiments, other filters may also be selected. Images can also be listed in the CBR system; these can include, for example, gross pathology or microscopic tissue micrograph images. Radiographic images can also be accessible using the CBR approach, and, as in the previous example, may be presented with positive findings shown as bars 810 to the +1 right side and negative findings as bars 805 to the −1 left side. These bars may be further distinguished by colors or other identifying aspects. Note that, according to the displayed embodiment, the message icon next to the urinalysis and uterus reports indicates that a pull down report is available for review with confirmation required on the uterus drill down report.

Figure 9:
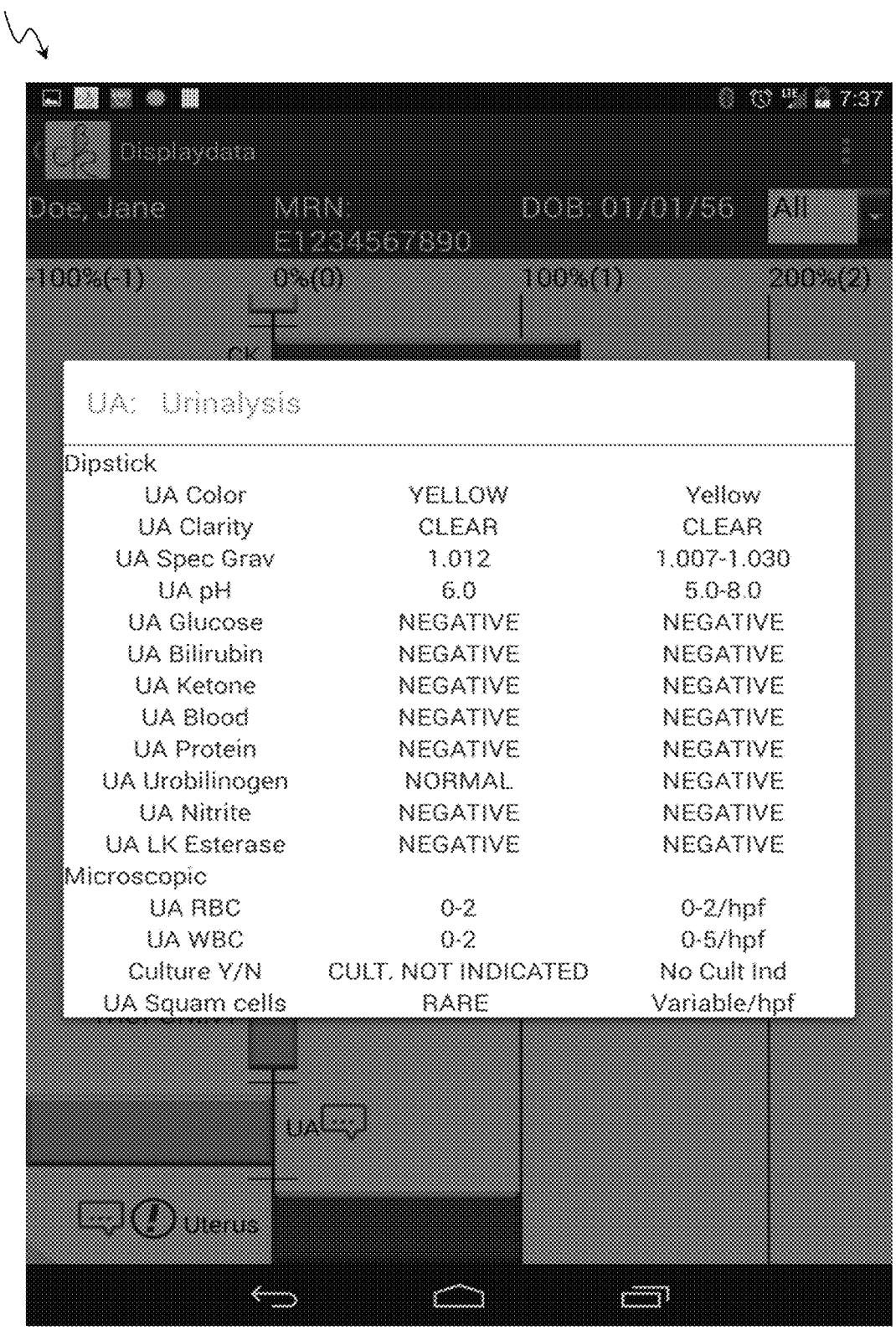
FIG. 9 is a GUI of an exemplary embodiment of software described herein.

Exemplary FIG. 9 provides a GUI 900 showing a report corresponding to the urinalysis test of exemplary FIG. 8, identified as a bar in the −1 direction in that example. Such a report may be displayed if a user touches or clicks the visual representation of the urinalysis test (such as the result bar of the previous example). In some alternative embodiments, the alert icon may be selected. The report may be accessed in other manners as would be understood by a person of ordinary skill in the art.

Figure 10:
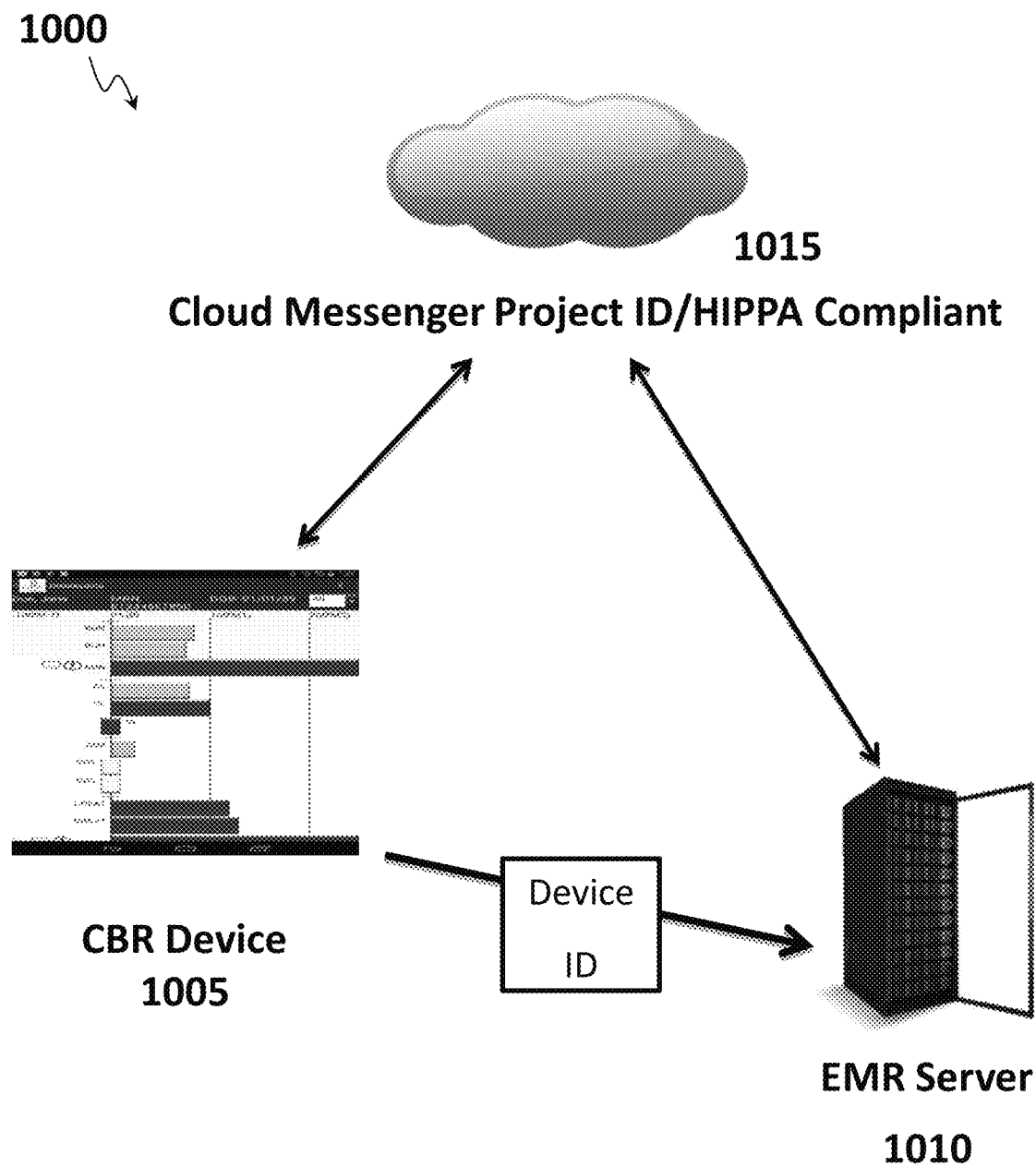
FIG. 10 is an exemplary diagram showing data flow associated with the software described herein.

Exemplary FIG. 10 is an illustration of a type of communication between a mobile device and software running thereon 1005, the electronic medical record server (EMR) 1010, and the cloud 1015, all in a HIPPA compliant network for secure information interchange. Mobile device 1005 may be required to pass a device ID to the EMR server 1010 before data may be interchanged, directly or indirectly, between the EMR server 1010 and the device 1005. Other proper project and device identifications may be required to be in place before medical information from the EMR 1010 may be sent to the device 1005 or before the EMR server 1010 will accept commands from the device 1005. Other restrictions may also be put in place; for example, devices 1005 may only be able to access the network from certain locations, or may not be able to run other software concurrently. Data may be stored on the cloud 1015, on the EMR server 1010, on a website database, and/or locally on the device 1005, as desired. A plurality of any of these elements may be incorporated into the same network; for example, the network may support a plurality of devices 1005, a plurality of cloud providers 1015, websites and website portals, and/or an EMR server cluster 1010. In an exemplary embodiment utilizing a website database, the database may be a web based PHP database with the medical information stored as an HL7 formatted message. A patient name and other unique identifiers, such as medical records number, social security number, telephone number, or other known unique identifiers, may be used as key fields to allow a device to identify and retrieve records through a patient portal. The records may be individual records or records of multiple encounters with a patient. In such an embodiment, the EMR server may automatically send patient data to the web database, allowing patients and physicians to pull data as desired, such as through a pull interface feature. This may reduce the time for retrieving desired data, by eliminating the need to go back to an EMR server.

Transfers of medical information may follow the HL7 approved standards for medical information interchange, or an alternative applicable standard. Transfers may incorporate communication elements such as the internet, the public switched telephone network (PSTN), other public and private networks, cellular links, satellite links, or any other communication channels desired. Communications may take place on the same network or may incorporate a plurality of networks; for example, different data transfers between devices may take place over different networks. Alternatively, certain devices may be able to transfer data over a plurality of networks in case one experiences a failure.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A computer-implemented method for receiving, storing, managing, and displaying medical results, comprising:
providing a mobile device configured to present a graphical user interface (GUI) on a display to a user, the user comprising a physician, medical practitioner, or patient;
providing an electronic medical records (EMR) server with a processor and a memory;
authenticating, by the processor, the device and user with the EMR server;
allowing, by the processor, the device to request data in the memory from the EMR server;
normalizing the data by the processor;
comparing the data with one or more threshold values by the processor;
transmitting, from the EMR server to the device, in response to at least one of a request provided to the EMR server by the device or an alert, a data set comprising medical information provided in the memory of the EMR server;
optimizing the normalized medical information for display on a mobile device, wherein optimizing the normalized medical information for display on the mobile device comprises formatting the medical data into a homogeneous format based on a predetermined preference value defining a default display and converting the medical data into one or more graph elements compatible with the GUI of the mobile device;
displaying the transmitted normalized medical information through the GUI on the mobile device;
prompting at least one of the physician, practitioner, or patient to take action based on the compared data via a prompt provided on the graphical user interface, and providing, in association with the prompt, a confirmation dialog, wherein further access to the graphical user interface is secured behind the confirmation dialog; and
combining the data with a user input, said user input comprising an identity of the at least one of the physician, practitioner, or patient.

2. The method of claim 1, wherein the medical data comprises patient test results from a plurality of medical tests.

3. The method of claim 2, wherein the graph elements are sized dynamically to fit on the display of the mobile device.

4. The method of claim 2, wherein a subset of the displayed medical information comprising medical test results is displayed in the form of a bar graph, and wherein elements of the bar graph are depicted differently to indicate medical test results that are within a normal range, close to the boundaries of normal range, or outside of normal range.

5. The method of claim 1, further comprising:
comparing the normalized medical data with one or more sets of previous medical data; and
automatically identifying medical trends for the patient based on the comparison of the normalized medical data with the one or more sets of previous medical data.

6. The method of claim 5, further comprising generating and transmitting an alert based on the identification of a medical trend.

7. The method of claim 1, wherein the GUI provides a plurality of normalized scales that are adjustable on three axes.

8. The method of claim 1, wherein the displayed GUI includes at least one icon associated with a subset of the transmitted medical information and which indicates at least one of the presence of a comment, the presence of additional information, or an alert.

9. The method of claim 1, wherein the GUI displays at least one medical test result and wherein additional medical information related to the at least one medical test result is displayed in response to user interaction with the at least one medical test result displayed on the GUI.

10. The method of claim 9, wherein the additional medical information comprises raw, non-normalized data, comments about a test, a normalized result, a method of analysis, and a facility where a test was performed.

11. The method of claim 1, wherein the device transmits to the EMR server at least one of the date, the time, the identity of the party currently associated with the device, and at least one medical record.

12. The method of claim 1, further comprising dynamically generating an overflow screen, the overflow screen displaying only normalized medical information above a threshold.

13. The method of claim 12, wherein the overflow screen is automatically displayed upon setting of a threshold value for at least one element in the normalized medical information.

14. The method of claim 12, where in the overflow screen is displayed following a swipe-right action if the overflow screen is dynamically generated and the overflow screen includes a fixed axis on a left portion of the screen with values from 0 to 100.

15. The method of claim 1, further comprising overlaying the transmitted normalized medical data on one or more sets of previously transmitted normalized medical data.

16. The method of claim 1, further comprising displaying a bar graph on the GUI with a fixed axis on a left side of the screen with values from 0 to 100.

* * * * *